United States Patent
Vermeulen et al.

(10) Patent No.: US 12,053,264 B2
(45) Date of Patent: *Aug. 6, 2024

(54) SYSTEM AND METHOD FOR MEASUREMENT SELECTION AND PROBE GUIDING IN A GINGIVITIS DETECTOR

(71) Applicant: KONINKLIJKE PHILIPS N.V., Eindhoven (NL)

(72) Inventors: Olaf Thomas Johan Antonie Vermeulen, Oss (NL); Lucas Petrus Henricus Scheffers, Utrecht (NL); Steven Charles Deane, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 734 days.

This patent is subject to a terminal disclaimer.

(21) Appl. No.: 17/274,921

(22) PCT Filed: Sep. 2, 2019

(86) PCT No.: PCT/EP2019/073295
§ 371 (c)(1),
(2) Date: Mar. 10, 2021

(87) PCT Pub. No.: WO2020/053003
PCT Pub. Date: Mar. 19, 2020

(65) Prior Publication Data
US 2022/0031169 A1    Feb. 3, 2022

Related U.S. Application Data

(60) Provisional application No. 62/729,460, filed on Sep. 11, 2018.

(51) Int. Cl.
A61B 5/00 (2006.01)
G01N 21/31 (2006.01)
G01N 21/47 (2006.01)

(52) U.S. Cl.
CPC .......... *A61B 5/0088* (2013.01); *A61B 5/0075* (2013.01); *A61B 5/7475* (2013.01);
(Continued)

(58) Field of Classification Search
CPC ... A61B 5/0075; A61B 5/0088; A61B 5/7475; G01N 21/314; G01N 21/4738; G01N 2021/3181
See application file for complete search history.

(56) References Cited

U.S. PATENT DOCUMENTS

2016/0232695 A1    8/2016    Berry et al.

FOREIGN PATENT DOCUMENTS

JP    2015177812 A    10/2015
JP    2016152933 A    8/2016
(Continued)

OTHER PUBLICATIONS

International Search Report and Written Opinion, International Application No. PCT/EP2019/073295, Mailed on Nov. 28, 2019.
(Continued)

*Primary Examiner* — Amelie R Davis

(57) ABSTRACT

A system (100) for detecting tissue inflammation, and gingivitis specifically, including a light emitter (102) configured to emit light at a tissue region (104) within a user's mouth; a light detector (106) configured to detect optical signals diffusely reflected through the tissue region over a period of time; a controller (130) configured to: determine a slope signal (Q) based on at least two signals ($R(\lambda_1)$, $R(\lambda_2)$) from the optical signals, the at least two signals including at least one signal from a hemoglobin-dominated wavelength range;
(Continued)

determine one or more characteristics of the slope signal; and select a best measurement signal based on the one or more characteristics of the slope signal. The system further includes a user interface (116) configured to provide information regarding a position of a probe for accurate detection of tissue inflammation based on the one or more characteristics of the slope signal.

20 Claims, 4 Drawing Sheets

(52) U.S. Cl.
CPC ....... *G01N 21/314* (2013.01); *G01N 21/4738* (2013.01); *G01N 2021/3181* (2013.01)

(56) References Cited

FOREIGN PATENT DOCUMENTS

| | | |
|---|---|---|
| JP | 2016535654 A | 11/2016 |
| JP | 2017000838 A | 1/2017 |
| JP | 2017131743 A | 8/2017 |
| JP | 2017153841 A | 9/2017 |
| WO | 2015069704 A1 | 5/2015 |

OTHER PUBLICATIONS

Stamatas, G. et al., "In vivo measurement of skin erythema and pigmentation: new means of implementation of diffuse reflectance spectroscopy with a commercial instrument", British Journal of Dermatology, Oxford, vol. 159, No. 3, Sep. 2008.

Denkceken, T. et al., "Elastic light single-scattering spectroscopy for the detection of cervical precancerous ex vivo", IEEE Transactions on Biomedical Engineering, vol. 60, No. 1, Jan. 2013.

Lobene, R. et al., "A modified gingival index for use in clinical trials", Clin. Prev. Dent. 8:3-6, 1986.

Hanioka, T. et al., "Hemoglobin concentration and oxygen saturation of clinically healthy and inflamed gingiva in human subjects", J. Periodontal Res. 25: 93-98, 1990.

SYSTEM AND METHOD FOR MEASUREMENT SELECTION AND PROBE GUIDING IN A GINGIVITIS DETECTOR

This application is the U.S. National Phase application under 35 U.S.C. § 371 of International Application No. PCT/EP2019/073295, filed on 2 Sep. 2019, which claims the benefit of U.S. Provisional Application No. 62/729,460, filed 11 Sep. 2018. These applications are hereby incorporated by reference herein.

FIELD OF THE INVENTION

The present disclosure is directed generally to oral healthcare systems and methods for improved detection of tissue inflammation, and gingivitis specifically, using diffuse reflected light.

BACKGROUND

Gingivitis detection using diffuse reflective spectroscopy (DRS) is currently performed with small, angled probes configured around one or more optical fibers which transport light due to the limited space in an oral cavity. Such small probes are useful for measuring at the interproximal areas where gingivitis commonly originates. However, when in contact, such small probes can exert a large pressure on the tissue, pushing away the blood and thereby disrupting the DRS measurement of blood properties. Thus, DRS measurements are preferably taken in non-contact mode and the required non-contact mode leads to detecting specular reflected light in addition to the desired diffuse reflected component. Since diffuse reflected light (i.e., light propagated through tissue) is highly attenuated, these specular components can become relatively large.

Furthermore, since gingivitis is predominantly found in locations that are hard to reach in the oral cavity, such as interproximal areas between the teeth, and at the back molars, in these positions it is practically impossible for a user to see how well a probe is aimed at the correct location (papillae).

Accordingly, there is a continued need in the art for inventive oral healthcare systems and methods for enabling more accurate gingivitis detection using DRS methods. The inventive oral healthcare systems and methods provide guidance to a user in probe positioning and/or facilitate selecting a best measurement from a continuous data stream.

SUMMARY OF THE INVENTION

The present disclosure is directed to inventive systems and methods for detecting tissue inflammation using diffuse reflective spectroscopy (DRS). Various embodiments and implementations herein are directed to an oral healthcare system configured to obtain measurements of gingival tissue to identify gingival inflammation. The oral healthcare system includes one or more light emitters, one or more light detectors, and a gingivitis detection system comprising a wavelength-sensitive slope detector configured to measure a reflected light slope from two or more wavelengths, where at least one wavelength is taken from a hemoglobin-dominated wavelength range. The system also includes a user feedback system and a measurement selection system driven by the wavelength-sensitive slope detector.

Generally, in one aspect, a method for detecting tissue inflammation is provided. The method includes emitting light by a light emitter towards a tissue region; detecting, via a light detector, optical signals diffusely reflected through the tissue region over a period of time; determining, by a controller, a slope signal based on at least two signals from the optical signals, the at least two signals including at least one signal from a hemoglobin-dominated wavelength range; determining, by the controller, one or more characteristics of the slope signal; and providing, via a user interface, information regarding a position of a probe for accurate detection of tissue inflammation based on the one or more characteristics of the slope signal. In various embodiments, the tissue inflammation is gingivitis.

In one embodiment, the step of determining the slope signal includes subtracting the at least two signals from each other.

In one embodiment, the one or more characteristics includes an increase or decrease in the slope signal which corresponds to whether the position of the probe is more or less accurate, respectively.

In one embodiment, the light emitter is a broadband light source and the light detector is a wavelength-dependent detector selected from the group consisting of a spectrometer, a tunable filter, or two or more discrete wavelength-sensitive photodetectors.

In one embodiment, the light emitter includes a plurality of light sources which are driven in a time sequential mode or driven simultaneously, where each light source of the plurality of light sources is modulated differently.

In one embodiment, the information includes feedback to a user or a third party.

In one embodiment, the method further includes the step of selecting a best measurement signal based on the one or more characteristics of the slope signal.

Generally, in another aspect, a method for detecting tissue inflammation is provided. The method includes emitting light by a light emitter towards a tissue region; detecting, via a light detector, optical signals diffusely reflected through the tissue region over a period of time; determining, by a controller, a slope signal based on at least two signals from the optical signals, the at least two signals including at least one signal from a hemoglobin-dominated wavelength range; determining, by the controller, one or more characteristics of the slope signal; and selecting, by the controller, a best measurement signal based on the one or more characteristics of the slope signal.

In one embodiment, the step of determining the slope signal includes subtracting the at least two signals from each other.

In one embodiment, the one or more characteristics includes a maximum value of the slope signal within the period of time.

In one embodiment, the method further includes the step of providing, via a user interface, information regarding a position of a probe for accurate detection of tissue inflammation based on the one or more characteristics of the slope signal.

In one embodiment, the information includes feedback to a user or a third party.

In one embodiment, the light emitter is a broadband light source and the light detector is a wavelength-dependent detector selected from the group consisting of a spectrometer, a tunable filter, or two or more discrete wavelength-sensitive photodetectors.

Generally, in another aspect, a system for detecting tissue inflammation is provided. The system includes a light emitter configured to emit light at a tissue region within a user's mouth; a light detector configured to detect optical signals diffusely reflected through the tissue region over a period of time; a controller configured to: determine a slope signal based on at least two signals from the optical signals, the at least two signals including at least one signal from a hemoglobin-dominated wavelength range; determine one or more characteristics of the slope signal; and select a best measurement signal based on the one or more characteristics of the slope signal; and a user interface configured to provide information regarding a position of a probe for accurate detection of tissue inflammation based on the one or more characteristics of the slope signal.

As used herein for purposes of the present disclosure, the term "controller" is used generally to describe various apparatus relating to the operation of an apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

Figure 1:
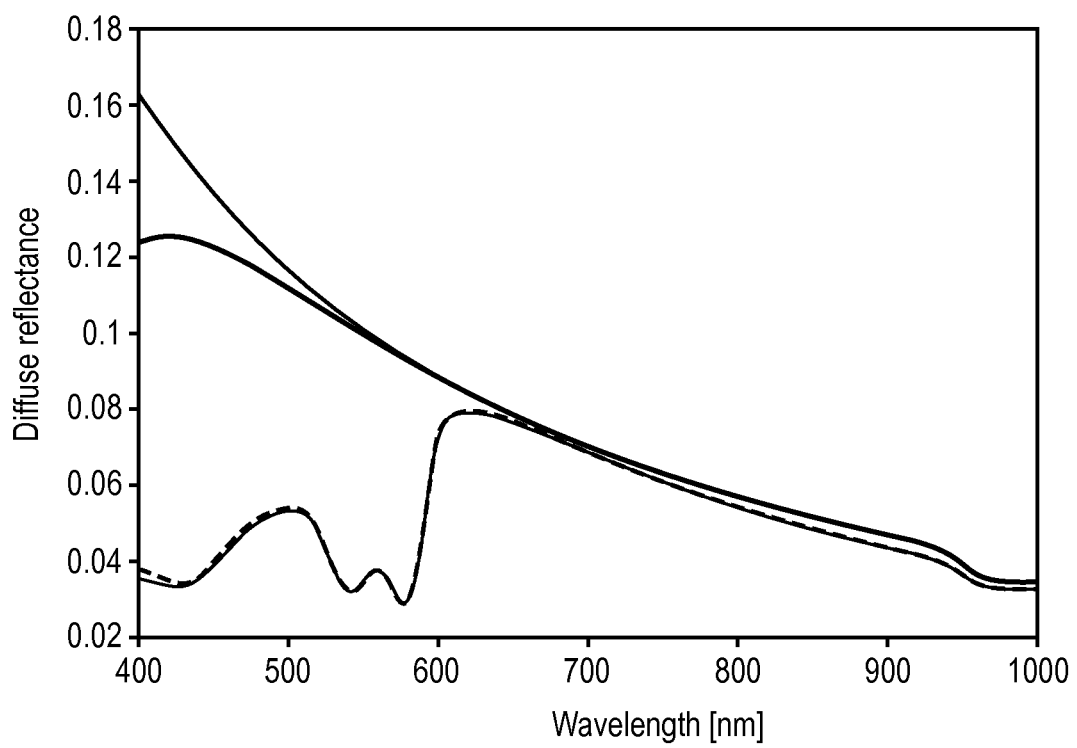
FIG. 1 is a graph of diffuse reflectance data, in accordance with an embodiment.

The present disclosure describes various embodiments of systems and methods for improved gingivitis detection using diffuse reflected light. More generally, Applicant has recognized and appreciated that it would be beneficial to provide a system to measure an amount of blood in gum tissue which corresponds to a presence of gingivitis. Accordingly, the systems and methods described or otherwise envisioned herein provide an oral healthcare device configured to obtain measurements of gingival tissue. The oral healthcare device includes a light emitter and a light detector configured to detect diffuse reflected light. Based on the reflectance data, the oral healthcare device can provide feedback to a user or a third party to allow optimized probe positioning. The reflectance data can also be used to select a best measurement.

The embodiments and implementations disclosed or otherwise envisioned herein can be utilized with any suitable oral healthcare device, such as a toothbrush, a flossing device, an oral irrigator, a tongue cleaner, or other personal care device. However, the disclosure is not limited to these oral healthcare devices, and thus the disclosure and embodiments disclosed herein can encompass any oral healthcare device.

Gingivitis, which is an inflammation of the gums, characterized by swollen gums, edema, and redness, is primarily caused by plaque build-up, mostly in the gingival sulcus (pockets). Such gum disease is typically found in areas that are hard to reach, such as interproximal areas between the teeth, and around the back teeth.

Indeed, it is estimated that 50%-70% of the adult population is affected by gingivitis. However, consumers are often unable to detect early signs of gingivitis. Typically, gingivitis progresses until individuals notice their gums easily bleeding when brushing their teeth. Accordingly, gingivitis may only be detected when the disease has already advanced and significantly harder to treat. Although gingivitis is readily reversed by improved oral hygiene, as gingivitis can propagate to irreversible periodontitis it is important to maintain good oral health and detect gingivitis as soon as possible.

Gingivitis may be visually diagnosed by detecting reddening and swelling of the gingiva. (see, R R. Lobene, et al., "A modified gingival index for use in clinical trials", Clin. Prev. Dent. 8:3-6, (1986) describing a non-contact gingivitis index, based on reddening and inflammation of the gingiva). However, this index has limited sensitivity and is highly dependent on the color rendering index of the light-source used. Thus, modern phosphor-converted light-emitting diodes (LEDs) can have a low CRI resulting in poor visual judgments.

The reddening of the gingiva is an acute inflammatory response to bacterial biofilm toxins from plaque in the gingivae sulcus or regions along the gum line. This inflammatory response in the short term causes vasodilation, where smooth muscle cells in the arterioles relax, and widen the blood vessels to increase blood supply to the capillary bed. This gives the reddening of the gingiva, and can give a small temperature increase, which is difficult to measure. In addition, the capillaries become more permeable, which results in increased fluid loss from the capillaries to the interstitial spaces, resulting in the swelling of the gums. If the inflammation is chronic, then additional reddening occurs by increased vascularization of the tissue, where additional capillaries may be formed to cope with the additional blood demands of the tissue.

These factors enable detection of gingivitis based on diffuse reflective spectroscopy (DRS). DRS is an optical method that involves emitting, for example, white light towards a target and analyzing spectral properties of the diffuse (rather than specular) reflected light. Due to the different chromophores in the gingival tissue, the spectral properties of the diffuse reflected light clearly differ from those of the source light. As described in T. Hanioka, et al., "Hemoglobin concentration and oxygen saturation of clinically healthy and inflamed gingiva in human subjects", J. Periodontal Res. 25: 93-98 (1990)), increased total-hemoglobin concentration and decreased blood oxygenation can be determined related to gingivitis detection. This method uses six fixed wavelengths and calculates deoxygenated-, oxygenated-, and total hemoglobin concentrations. The latter two are used to calculate oxygen saturation.

A particular goal of utilization of certain embodiments of the present disclosure is to provide feedback to a user to allow optimized probe positioning and thereby allow more accurate gingivitis detection. The feedback is based on an amount of blood measured and is independent of specular reflection. The amount of blood measured is also used to select the best measurement.

As discussed above, DRS-based gingivitis detection is based on increased total hemoglobin concentration or decreased oxygen saturation. Both of these parameters are dependent on oxygenated and de-oxygenated hemoglobin concentrations. It is therefore beneficial to steer the probe position such that a maximum amount of hemoglobin components is detected.

FIG. 1 shows a measured DRS signal with fitted spectra of other components. The other components include a tissue scattering component, the top line in the chart, which is the component that enables the diffuse reflectance (i.e., without it, no light would be diffusely reflected/returned) and the absorption component due to melanin which is one of the main absorbing chromophores in gingival tissue (the middle line in the chart). The DRS spectrum shown in FIG. 1 does not contain a specular reflection component (or very little). The DRS spectrum can be separated into two wavelength ranges: a first wavelength range that is below approximately 615 nm where the absorption spectrum is dominated by hemoglobin and a second wavelength range that is above approximately 615 nm where the absorption spectrum is dominated by the tissue component. The hemoglobin-dominated region is best suited for determining an amount of the DRS signal originating from blood. The bottom line in the chart, the dotted line, shows the measurement that includes hemoglobin (blood) and melanin.

Figure 2A:
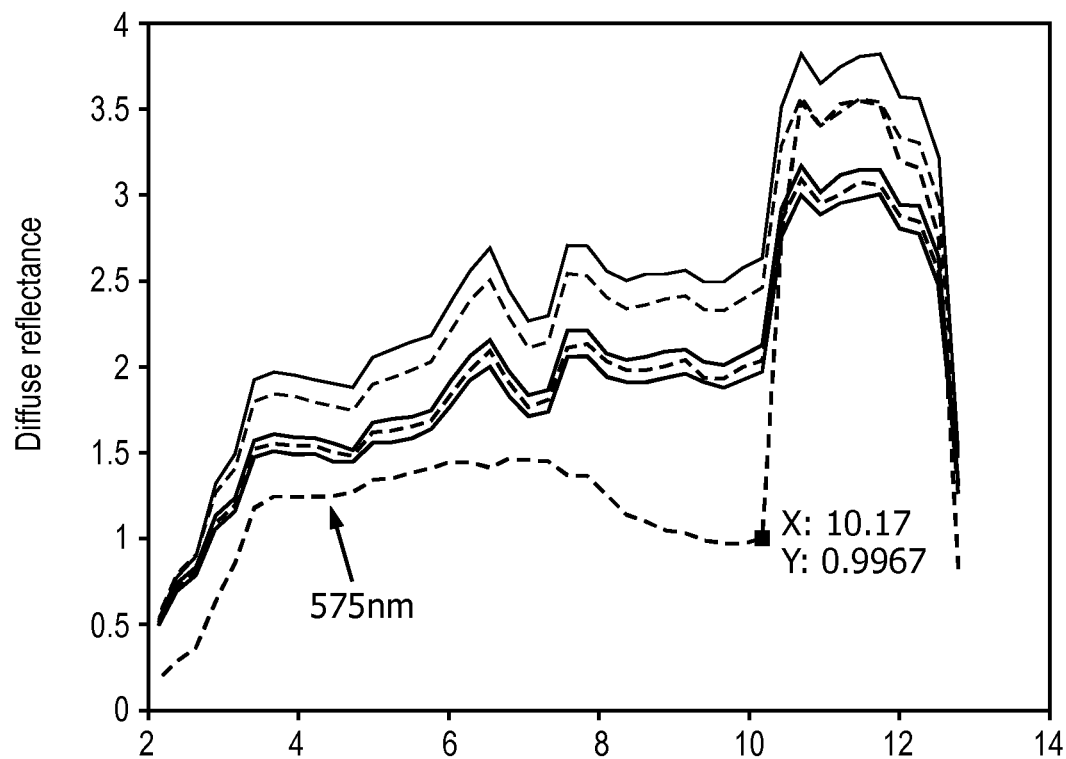
FIG. 2A is a graph of diffuse reflectance data for six wavelengths, in accordance with an embodiment.

In FIG. 2A, a time sequence of DRS signals is measured at six wavelengths. The measurements shown in FIG. 2A are taken while a DRS probe is being positioned towards the gingiva. The following observations are noted in FIG. 2A: at <7 seconds, the signals all show more or less the same upward trend. The signal from the hemoglobin-dominated region (i.e., 575 nm, the bottom line in the chart) shows the biggest deviation from the trend. At greater than 7.5 seconds and less than 10.17 seconds, the probe now approaches the gingiva in such a way that the diffuse reflected light starts to be influenced by hemoglobin (the 575 nm signal drops because of absorption while the others keep increasing). This trend continues until at 10.17 seconds when the probe touches the gingiva. At greater than 10.17 seconds and less than 12.5 seconds, the probe is pushing away blood and the 575 nm signal increases. At greater than 12.5 seconds, the probe is removed.

From this time sequence, it might seem that the level of a signal from the hemoglobin-dominated region may be adequate to function as a measurement quality signal, useable for measurement selection and user feedback. However, it is unknown how much specular reflection is in the signals. Since it is achromatic, specular reflection might appear or it might not. Similarly, specular reflection might be present or it might not. Thus, using the level of a signal from the hemoglobin-dominated region to function as a measurement quality signal is not adequate.

Figure 2B:
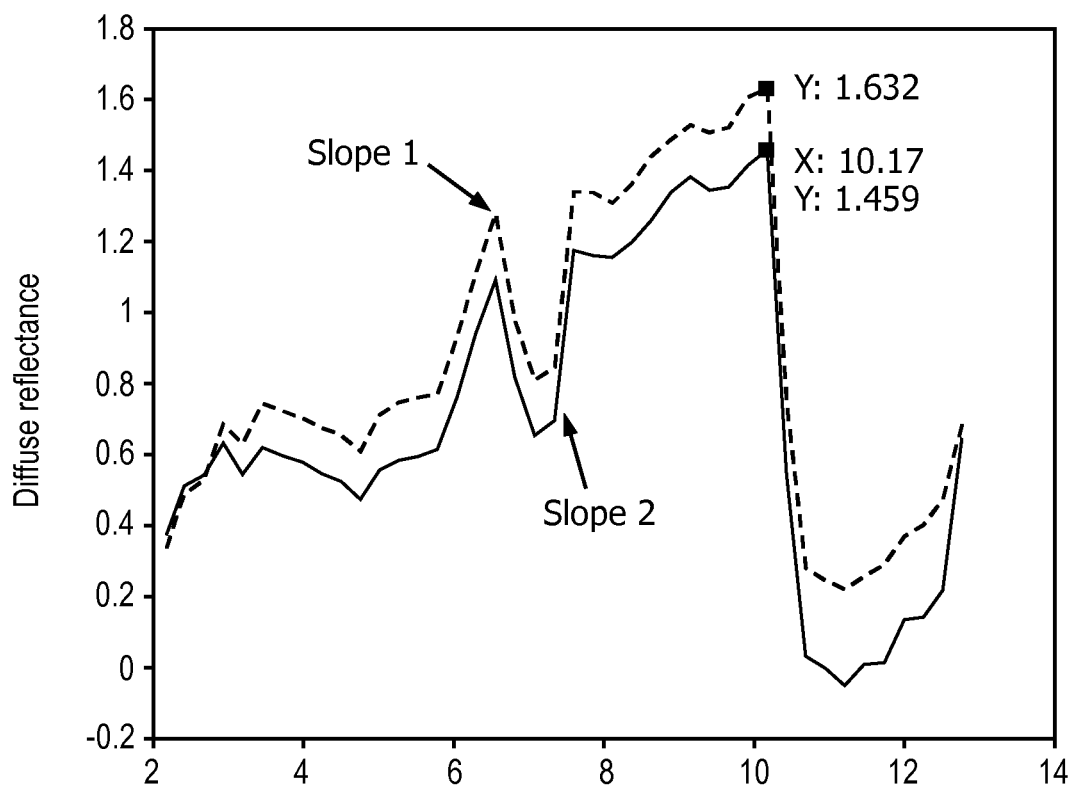
FIG. 2B is a graph of two computed slopes, in accordance with an embodiment.

In FIG. 2B, two slopes are shown. Each slope is computed from a wavelength in the hemoglobin-dominated region and a wavelength from the tissue-dominated region. For example, slope 1 represents the 575 nm signal subtracted from the 630 nm signal and slope 2 represents the 575 nm signal subtracted from the 674 nm signal. Thus, the two wavelengths used for each computation are from either side of 615 nm signal in the embodiment depicted. Thus, the inventive systems and methods described herein function with different tissue wavelengths. Both slopes show the same trend because all signals with a wavelength from the tissue-dominated region show very little difference between each other. Since these signals are independent of specular reflection, they are therefore an appropriate signal quality indicator.

Figure 3:
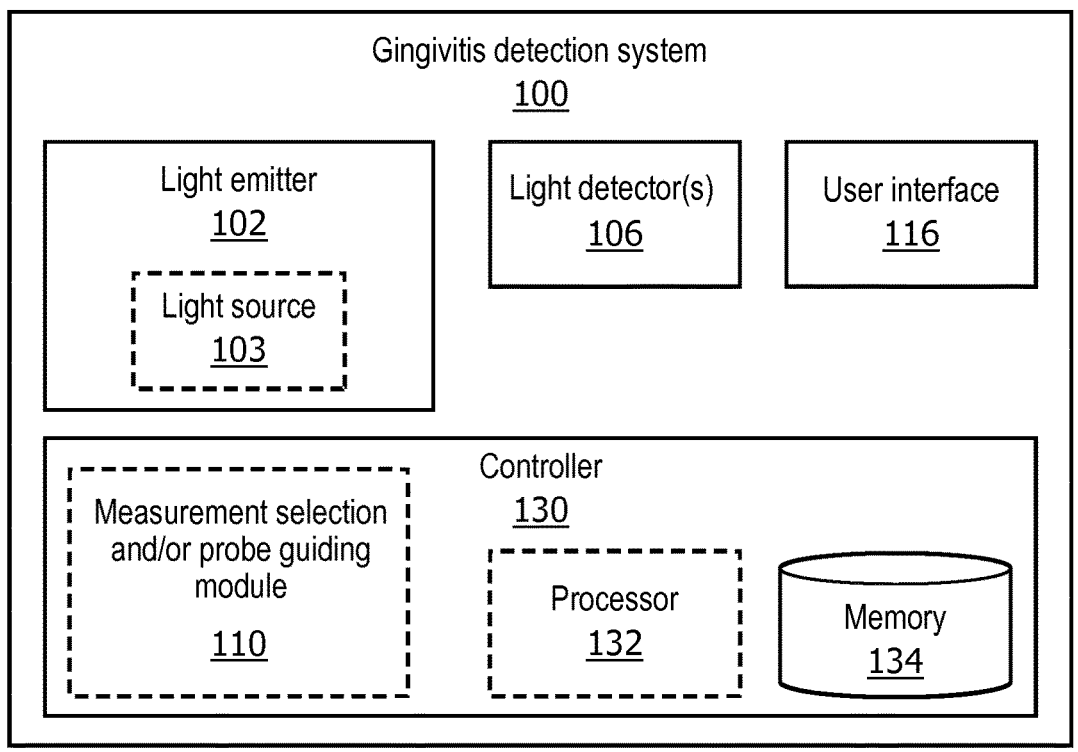
FIG. 3 is a schematic representation of a gingivitis detection system, in accordance with an embodiment.
Figure 4:
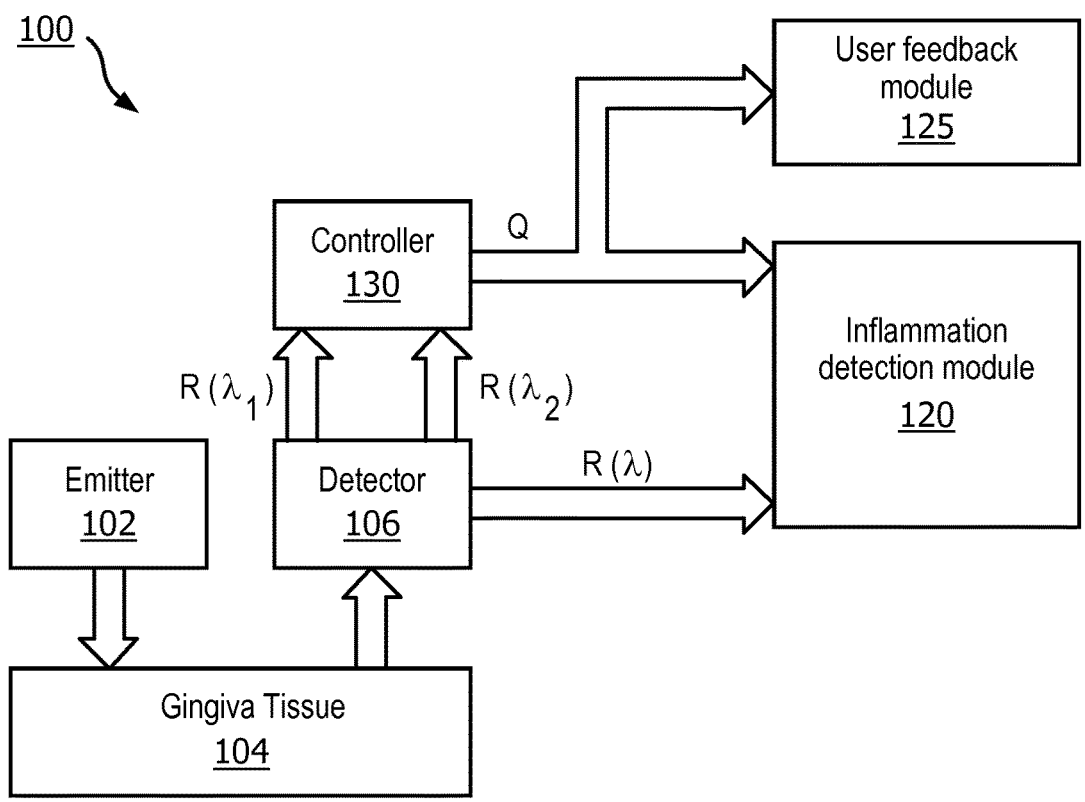
FIG. 4 is a schematic representation of a gingivitis detection system, in accordance with an embodiment.

Based on the above and referring to FIGS. 3 and 4, in one embodiment, is a system 100 for detecting tissue inflammation, and gingivitis specifically. The system 100 includes a light emitter 102 comprising, for example, a broadband light source 103 or any suitable alternative. According to an embodiment, the light source 103 is a phosphor-converted white LED coupled into a source fiber configured to deliver the emitted light to a tissue region 104 within a user's mouth. The system 100 also includes a light detector 106 configured to pick up diffuse reflected light from tissue region 104. According to an embodiment, the light detector 106 comprises a wavelength-dependent light detector (e.g., spectrometer, tunable filter or discrete wavelength-sensitive photodetectors). According to an embodiment, the light detector is a fiber configured to direct the diffuse reflected light to one or more wavelength-dependent detectors.

System 100 also includes a controller 130 comprising a processor 132 and a memory 134. In one embodiment, a single controller is sufficient. In other embodiments, two or more separate controllers are included to carry out the different functions. The wavelength-dependent light detector 106 is configured to generate and transmit reflectance data to the one or more controllers 130 and/or an inflammation detection module 120. The controller 130 includes measurement selection and/or probe guiding module 110 configured to analyze the reflectance data from the wavelength-dependent light detector 106 and determine a slope signal which functions as a quality signal. Using the quality signal, the module 110 is further configured or programmed to provide information for positioning a DRS probe for accurate gingivitis detection. System 100 can also include a user interface 116 configured to provide such guidance information to a user based on information from the measurement selection and/or probe guiding module 110. For example, user interface 116 can be or comprise a user feedback module 125 that provides direct feedback to a user, e.g., by increasing a repetition rate of a pulsed signal (audible or visual), colorbar or tone.

Additionally or alternatively, the module 110 is configured or programmed to select a best measurement from a set of measurements over a period of time. According to one embodiment, the set of measurements comes from a single detector. According to another embodiment, the set of measurements comes from two or more detectors. According to an embodiment, the module 110 is configured to select a best measurement and guide a user at the same time.

While the system can include a single broadband light emitter 102 and two or more wavelength-dependent light detectors 106, the system can alternatively include two or more light emitters 102 which are driven in time sequential mode to generate the wavelength-diverse part at the source and a single wavelength-independent detector. According to still another embodiment, the system can include two or more light sources which are driven at the same time but modulated differently such that a single wavelength-independent detector can lock-in into each light source separately.

According to an embodiment, system 100 can be implemented as any oral healthcare device configured to come into proximity with gingiva that can be quantified. For example, system 100 can be implemented as any oral healthcare device such as an electric toothbrush, a flossing device, an oral irrigator, a tongue cleaner, or any other oral inspection device.

Figure 5:
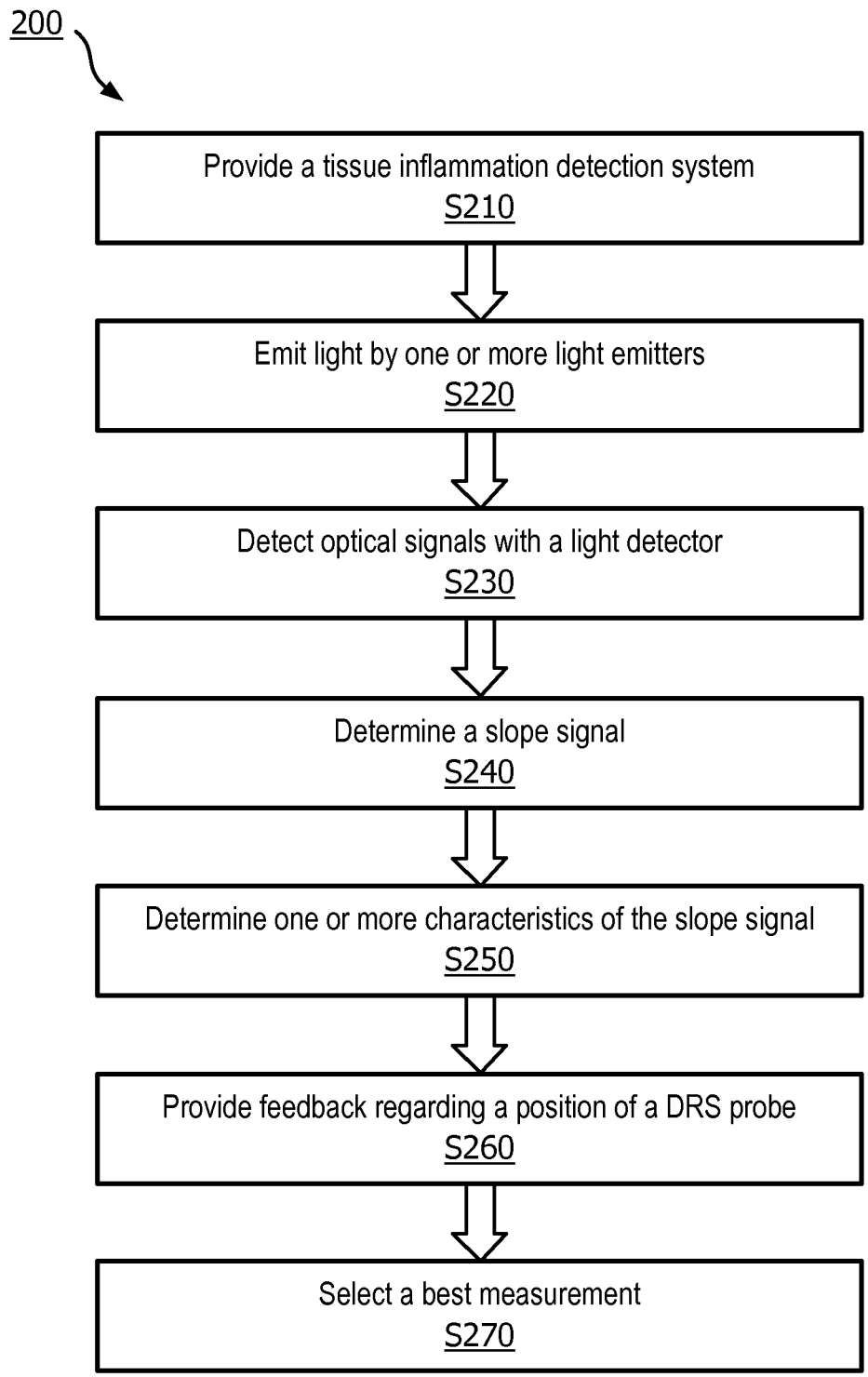
FIG. 5 is a flowchart of a method for detecting gingivitis, in accordance with an embodiment.

Referring to FIG. 5, in one embodiment, is a flowchart of a method 200 for measurement selection and/or probe guiding using a gingivitis detector. In step S210, a system for detecting tissue inflammation, and gingivitis specifically, is provided. The system may be any of the devices or systems described or otherwise envisioned herein. Generally, the system includes one or more light emitters 102, one or more light detectors 106, and one or more controllers 130 configured to analyze the reflectance data from the one or more light detectors. Many other components and configurations are possible.

At step S220 of the method, at least one light emitter 102 emits light, a beam of which impacts a tissue region within a user's mouth. The light emitted by the light emitter can include two or more wavelengths. Accordingly, the light emitter may comprise one or more light sources. The light emitter may emit light periodically or continuously, or may emit light only in response to a trigger. For example, the system detects gingival tissue and activates light emitter 102 to emit light.

At step S230 of the method, one or more light detectors 106 obtains reflectance data, such as diffuse reflectance from the tissue region reflecting light emitted by the light emitter 102. The light detector may obtain a single data point or may obtain multiple data points over time. The light detector may obtain data periodically or continuously, or may only obtain data in response to a trigger. For example, the light detector may be triggered to obtain sensor data in response to activation of a light emitter. According to an embodiment, a continuous data stream over a period of time is obtained while a user is using the inflammation detection system and such continuous data stream can be used for properly positioning a DRS probe. According to another embodiment, the continuous data stream can be used to select a best measurement. According to another embodiment, the continuous data stream can be used to properly position a DRS probe and select a best measurement.

According to an embodiment, system 100 includes a DRS probe having a source-detector separation of greater than 300 μm. According to one embodiment, one or more light sources 103 are coupled into a source fiber of the probe to deliver light and a detector fiber directs the diffuse reflected light to one or more wavelength-dependent detectors 106. Typical configurations include one source fiber next to one detection fiber, one central source fiber surrounded by a plurality of detection fibers, or a single fiber functioning as source and detector simultaneously. An important property of the probe is the source-detection separation because it influences the sampling depth of the probe (i.e., from how deep in the tissue the measured light originates). To detect gingivitis, an average diffuse reflective spectroscopy sampling depth that is greater than 250 μm is required. To obtain such an average, a minimum source-detector distance of approximately 300 μm is required, depending on wavelength.

According to an embodiment, the light detector obtains data continuously for a time series of measurements. In an embodiment, the series of measurements can be taken from a single location with changing conditions. For example, the changing condition can include a changing distance as a user moves a DRS probe closer to gingival tissue at a single detection spot. By way of another example, the changing condition can be, e.g., the introduction or removal of saliva, toothpaste or any other oral substance between the DRS probe and the gingiva at a single detection spot. The series of measurements can alternatively be taken from different locations as a user moves a DRS probe among different detection spots within a user's mouth. The series of measurements corresponding to different locations can alternatively be obtained with multiple detectors positioned over differing detection spots versus a single detector moving among different detection spots.

At step S240 of the method, the controller 130 receives the obtained reflective data where it is analyzed by processor 132 to obtain a slope signal Q corresponding to measurement quality. Additionally or alternatively, the obtained reflective data is stored in memory 134 for future analysis. According to an embodiment, the controller 130, which can be implemented as an algorithm, analyzes the obtained reflectance data in one or more steps. As a first initial step, the controller 130 identifies signals from two or more wavelengths including at least one signal from a hemoglobin-dominated wavelength range (i.e., <615 nm). As discussed above by way of example, since the absorption spectra of the tissue scattering component and the melanin component in a wavelength range below approximately 615 nm vary considerably from the absorption spectra of hemoglobin, the two can be distinguished. As a second step, the controller computes a reflected light slope signal by subtracting the two signals from each other (i.e., $R(\lambda_1)-R(\lambda_2)$ as shown in FIG. 4). The reflected light slope signal represents the measurement quality signal Q. The measured slope signal Q can be stored in memory 134 for future use.

At step S250 of the method, the controller 130 analyzes the slope signal Q to determine one or more characteristics. In an embodiment, the controller 130 can analyze the slope signal to determine an absolute value, for example, a maximum value over a period of time. Additionally or alternatively, the controller 130 can analyze the slope signal to determine a relative value (i.e., a change in slope compared to a reference at a previous time), for example, increasing or decreasing.

At step S260 of the method, information regarding a position of a DRS probe is provided via user interface 116 based on the one or more characteristics. User interface 116 can provide direct and/or indirect feedback to the user while an oral healthcare device or system is in use so that the user can accurately position the oral healthcare device. According to an embodiment, the information provided to the user is based on a relative value determined by the controller 130 in real-time. For example, an increasing or decreasing slope signal determined by the controller 130 can indicate that the position of the DRS probe is becoming better or worse, respectively. In the example depicted in FIG. 2B, an increasing slope indicates the position of the DRS probe is improving while a decreasing slope indicates the position is worsening. Thus, in the example of FIG. 2B, when a user positions a DRS probe toward the gingiva and advances the probe toward the gingiva, the user interface can provide feedback based on the analysis of the slope signal indicating that such movement constitutes improvements in the positioning of the DRS probe.

At step S270 of the method, a best measurement can be selected based on the one or more characteristics. For example, a time within a time series of measurements at which a maximum occurred can be used for selecting a best measurement signal. Referring to FIG. 2B for example, the highest value for either slope (i.e., around 10.17 seconds), which is immediately before the probe contacts the gingiva, can be selected as a best measurement. A selected best measurement can be used by the inflammation detection module 120 to calculate, e.g., oxygenation values, for determining a gingivitis status. Such module 120 is configured or programmed to receive a selected best measurement from the controller 130. According to an embodiment, each time a gingivitis status is calculated, the corresponding value of a slope signal Q is compared with a previously stored best (highest slope) result. When the slope signal is higher, the new gingivitis and slope signals can be stored in memory 134.

In embodiments directed to selecting a best measurement without providing probe positioning guidance, step S270 occurs in place of step S260. Similarly, in embodiments directed to providing probe positioning guidance without selecting a best measurement, step S270 is omitted. In embodiments directed to providing probe positioning guidance and selecting a best measurement, steps S260 and S270 can occur simultaneously or sequentially.

Advantageously, the inventive systems and methods described herein combine a user feedback signal and a measurement quality signal. Accordingly, the inventive systems and methods enable a user to precisely position a DRS probe and/or select a best measurement for enabling more accurate gingivitis detection.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A system for detecting tissue inflammation, comprising:
   a light emitter configured to emit light at a tissue region within a user's mouth;
   a light detector configured to detect optical signals diffusely reflected through the tissue region over a period of time;
   at least one controller, characterized in that the controller is configured to:
      determine a first difference signal (Q) based on a difference between at least two signals ($R(\lambda_1)$, $R(\lambda_2)$) from optical signals of different wavelengths among the optical signals diffusely reflected through the tissue region over the period of time, the at least two signals comprising at least one signal from a hemoglobin-dominated wavelength range and at least one from above the hemoglobin-dominated wavelength range;
      determine one or more characteristics of the first difference signal; and
      select a best measurement signal from the optical signals based on the one or more characteristics of the first difference signal; and
   a user interface configured to provide information regarding a position of a probe for accurate detection of tissue inflammation based on the one or more characteristics of the first difference signal from the best measurement signal.

2. The system of claim 1,
   wherein the light emitter is a broadband light source, and the light detector is a wavelength-dependent light detector selected from the group consisting of a spectrometer, a tunable filter, and two or more discrete wavelength-sensitive photodetectors.

3. The system of claim 2,
   wherein the broadband light source comprises a phosphor-converted white light-emitting diode coupled into a source fiber.

4. The system of claim 2,
   wherein the at least one controller further comprises a measurement selection and/or probe guiding module configured to analyze reflectance data from the light detector and determine a second difference signal which functions as a quality signal,
   wherein the user interface is configured to at least one of select the best measurement signal or provide the information regarding the position of the probe based on the second difference signal which functions as a quality signal.

5. The system of claim 1, further comprising:
   an inflammation detection module configured to receive the best measurement signal from the at least one controller and calculate oxygenation values to determine a gingivitis status.

6. The system of claim 1,
   wherein the user interface further comprises a user feedback module to provide the information regarding the position of the probe as feedback to a user.

7. The system of claim 1, further comprising:
   two or more wavelength-dependent light detectors including the light detector.

8. The system of claim 1, further comprising:
   two or more light emitters, including the light emitter, and configured to be driven in time sequential modes,
   wherein the light detector is a wavelength independent light detector.

9. The system of claim 1, wherein the user interface is configured to provide the information regarding the position of the probe in real-time as the light emitter emits light at the tissue region and as the light detector detects the optical signals diffusely reflected through the tissue region.

10. The system of claim 1, wherein the first difference signal comprises a slope, and the information regarding the position of the probe for accurate detection of tissue inflammation is based on a change in the first difference signal which reflects whether positioning of the probe for accurate detection of tissue inflammation is improving or worsening.

11. A method for detecting tissue inflammation, the method comprising:
   emitting light by a light emitter towards a tissue region; and
   detecting, via a light detector, optical signals diffusely reflected through the tissue region over a period of time,
   characterized in that the method comprises:
   determining, by a controller, a first difference signal (Q) based on a difference between at least two signals ($R(\lambda_1)$, $R(\lambda_2)$) from the optical signals of different wavelengths among the optical signals diffusely reflected through the tissue region over the period of time, the at least two signals comprising at least one signal from a hemoglobin-dominated wavelength range and at least one from above the hemoglobin-dominated wavelength range;
   determining, by the controller, one or more characteristics of the first difference signal; and
   providing, via a user interface, information regarding a position of a probe for accurate detection of tissue inflammation based on the one or more characteristics of the first difference signal.

12. The method of claim 11,
   wherein the tissue inflammation is gingivitis.

13. The method of claim 11,
   wherein determining the first difference signal comprises subtracting the at least two signals from each other.

14. The method of claim 11,
   wherein the light emitter comprises a plurality of light sources which are driven in a time sequential mode or driven simultaneously, where each light source of the plurality of light sources is modulated differently.

15. The method of claim 11,
   wherein the information regarding the position of the probe comprises feedback to a user or a third party provided to the user of the third party.

16. The method of claim 11, further comprising:
   selecting a best measurement signal from the optical signals based on the one or more characteristics of the first difference signal,
   wherein the information regarding the position of the probe for accurate detection of tissue inflammation based on the one or more characteristics of the first difference signal is provided via the user interface from the best measurement signal.

17. The method of claim 11, wherein the one or more characteristics comprises a maximum value of the first difference signal within the period of time.

18. The method of claim 11, wherein the user interface is configured to provide the information regarding the position of the probe in real-time as the light emitter emits light at the tissue region and as the light detector detects the optical signals diffusely reflected through the tissue region.

19. The method of claim 11, wherein the first difference signal comprises a slope, and the information regarding the position of the probe for accurate detection of tissue inflammation is based on a change in the first difference signal which reflects whether positioning of the probe for accurate detection of tissue inflammation is improving or worsening.

20. A tangible non-transitory computer readable storage medium in a system for detecting tissue inflammation with a controller, a light emitter, a light detector, a user interface and a probe, the computer readable storage medium storing a computer program that, when executed by the controller, cause the system to:

determine a first difference signal (Q) based on a difference between at least two signals ($R(\lambda_1)$, $R(\lambda_2)$) from optical signals of different wavelengths among the optical signals diffusely reflected through a tissue region over a period of time, the at least two signals comprising at least one signal from a hemoglobin-dominated wavelength range and at least one from above the hemoglobin-dominated wavelength range;

determine one or more characteristics of the first difference signal;

select a best measurement signal from the optical signals based on the one or more characteristics of the first difference signal; and generate information for the user interface regarding a position of a probe for accurate detection of tissue inflammation based on the one or more characteristics of the first difference signal from the best measurement signal.

* * * * *